United States Patent [19]
Widlund

[11] Patent Number: 5,690,625
[45] Date of Patent: Nov. 25, 1997

[54] ABSORBENT DISPOSABLE ARTICLE CONSTRUCTED FROM AT LEAST TWO PLAT FLEXIBLE BODIES CONTAINING ABSORBENT MATERIAL, AND A PACKAGE OF ARTICLES HAVING S-SHAPED EDGES

[75] Inventor: Urban Widlund, Mölnlycke, Sweden

[73] Assignee: Molnlycke AB, Gothenburg, Sweden

[21] Appl. No.: 766,935

[22] Filed: Dec. 16, 1996

Related U.S. Application Data

[63] Continuation of Ser. No. 284,405, filed as PCT/SE93/00120, Feb. 16, 1993, abandoned.

[30] Foreign Application Priority Data

Feb. 18, 1992 [SE] Sweden .................... 9200482

[51] Int. Cl.⁶ .................... A61F 13/15; A61B 17/06
[52] U.S. Cl. .................... 604/385.1; 604/387; 206/438
[58] Field of Search .................... 604/385.1–387, 604/389–391

[56] References Cited

U.S. PATENT DOCUMENTS

| | | |
|---|---|---|
| 3,527,221 | 9/1970 | Croon . |
| 3,875,837 | 4/1975 | Dussaud . |
| 3,884,234 | 5/1975 | Taylor . |
| 3,884,243 | 5/1975 | Cywinski . |
| 4,631,062 | 12/1986 | Lassen et al. .......... 604/385.1 |
| 4,655,759 | 4/1987 | Romans-Hess et al. . |
| 4,743,245 | 5/1988 | Lassen et al. .......... 604/385.1 |
| 4,804,380 | 2/1989 | Lassen et al. .......... 604/385.1 |
| 5,171,302 | 12/1992 | Buell .......... 604/385.1 |
| 5,197,959 | 3/1993 | Buell .......... 604/385.1 |

FOREIGN PATENT DOCUMENTS

| | | |
|---|---|---|
| 0 302 523 | 2/1989 | European Pat. Off. . |
| 302 523 | 2/1989 | European Pat. Off. . |
| 1 883 806 | 12/1963 | Germany . |
| 5208034 | 8/1993 | Japan .......... 604/385.1 |
| 121859 | 3/1968 | Norway . |
| 121598 | 5/1969 | Norway . |
| 7310474-7 | 5/1976 | Sweden . |
| 1570544 | 7/1980 | United Kingdom . |
| 2057266 | 4/1981 | United Kingdom . |
| 86/06620 | 11/1986 | WIPO . |

Primary Examiner—John G. Weiss
Assistant Examiner—K. M. Reichle
Attorney, Agent, or Firm—Burns, Doane, Swecker & Mathis LLP

[57] ABSTRACT

The present invention relates to an absorbent disposable article, such as a sanitary napkin, a panty protector, or a diaper. The article includes at least two generally flat, flexible bodies which include absorbent material and which, in a packaging state, can lie against one another with first flat sides which are intended to face toward the wearer when the article is in use. Two neighboring bodies of the article are mutually joined along a first common edge which forms a folding line around which the bodies can be folded out from their packaging state and which includes an arcuate section which, in the packaging state of the article, is arched toward a second opposing edge of the bodies.

12 Claims, 3 Drawing Sheets

ABSORBENT DISPOSABLE ARTICLE CONSTRUCTED FROM AT LEAST TWO PLAT FLEXIBLE BODIES CONTAINING ABSORBENT MATERIAL, AND A PACKAGE OF ARTICLES HAVING S-SHAPED EDGES

This application is a continuation of application Ser. No. 08/284,405, filed as PCT/SE93/00120, Feb. 16, 1993 now abandoned.

BACKGROUND OF THE INVENTION

The present invention relates to an absorbent disposable article, such as a sanitary napkin, a panty protector, a diaper or an incontinence guard.

Such articles are normally flat, i.e. have a two-dimensional shape, and are manufactured from flexible material. Although the flat shape of such articles is convenient from the technical aspect of manufacture, a flat article cannot readily be caused to conform to the shape of the wearer's anatomy. Because a poorly-fitting article will, in many cases, give rise to leakage and subsequent discolouring of the wearer's underclothes, various attempts have been made to produce articles of the aforesaid kind which will adapt better to the shape of the wearer's anatomy. For instance, the flat articles have been provided in manufacture with pre-stretched elastic which, when contracting, forces the two-dimensional article to take a three-dimensional shape. One advantage with this solution is that the articles can be packed in a flat state, although the provision of elastication results in more complicated and expensive manufacture.

Another solution for providing a three-dimensional shape in sanitary napkins or like articles is to impart the desired shape to the sanitary napkin during the manufacturing process. An example of this solution is given in EP-A2-0302523. One drawback with this solution is that articles which are three-dimensional from the beginning are relatively expensive to manufacture and, consequently, the purchase price of such articles is relatively high.

OBJECTS AND SUMMARY

An object of the present invention is to provide an absorbent disposable article which has a flat packaging state and a three-dimensional state of use and which in its state of use will conform effectively with the shape of the wearer's body.

According to an aspect of the invention, a preferred embodiment of an absorbent disposable article of the aforesaid kind comprises at least two essentially flat, flexible bodies which include absorbent material. The two bodies have first flat sides which can lie against one another in a packaging state and which when the article is worn face towards the wearer. The two bodies of the article are mutually joined along a first common edge which forms a folding line around which the bodies can be unfolded from their packaging state, and which includes an arcuate section which in the packaging state of the article is arched towards a second, opposing edge of the bodies. An article of this kind can be manufactured generally in the same manner as conventional flat articles and may also be packed flat, with the inner surfaces of the bodies of the article in mutual abutment with one another. When the absorbent bodies of the article are folded out from their packaging state so as to mutually separate the abutting sides of the bodies, there is formed a three-dimensional article which has a part which is outwardly concave, i.e., inwardly convex or curved toward the wearer, within the region of the arcuate section. This outwardly concave part can readily be fashioned to a full or a partial outwardly convex configuration with a simple hand movement, whereupon the article within this manually curved area obtains a cross-sectional shape in the form of an inverted V. A sanitary napkin having a part which is shaped in this way will fit snugly around the wearer's body, within the region where the buttocks meet.

BRIEF DESCRIPTION OF THE DRAWINGS

The invention will now be described in more detail with reference to a preferred embodiment thereof and also with reference to the accompanying drawings, in which.

DETAILED DESCRIPTION OF THE PREFERRED EMBODIMENTS

Figure 1:
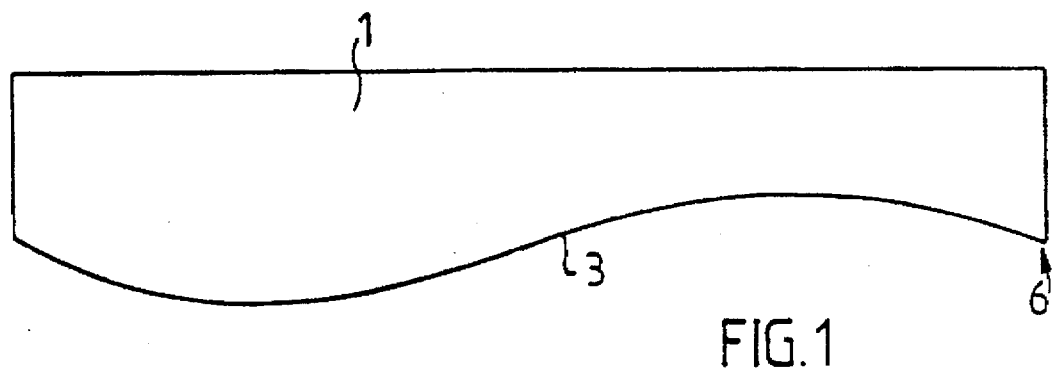
FIG. 1 is a side view of an inventive absorbent article.

FIGS. 1–4 illustrate schematically a sanitary napkin configured in accordance with a preferred embodiment of the invention. The illustrated napkin includes two elongated, mirror-symmetrical absorbent bodies 1, 2, of which only the body 1 can be seen in FIG. 1. The bodies 1, 2 are mutually joined along an S-shaped edge 3 which extends in the longitudinal direction of the napkin. The S-shaped edge 3 has a first arcuate section 5, which is arched towards the opposing straight edge of the bodies 1, 2 shown uppermost in FIG. 1. This may also be expressed as this edge section 5 being outwardly concave, since in FIGS. 1–4 the outside of the napkin is show facing downwardly. The remainder of the S-shaped edge 3 is formed by a second arcuate section 4 which is arched away from the opposing straight edge or is, in other words, outwardly convex.

The bodies 1, 2 are preferably constructed in a conventional manner, i.e., with an absorbent pad 10 (shown by dotted lines) enclosed between an inner liquid-permeable casing sheet 11 which in use lies nearest the wearer's skin and an outer liquid-impermeable casing sheet 12 (FIG. 2), although it can also be made of homogenous bonded material. As opposed to the thin elastic casing materials normally used to produce flat absorbent pads for diapers, sanitary napkins or incontinence guards, the outer casing sheet included in the bodies 1, 2 may include a much stiffer, cheaper material, which does not need to be elastic. The stiffness of this material, however, will preferably not prevent the material from being wound onto and unwound from a material roll so as to enable a web of outer sheet material used in accordance with the invention to be used in the manner conventional in the manufacture of flat absorbent disposable articles.

Hydrophobic non-woven material or plastic film, for instance polyethylene film, are suitable outer casing materials.

The inner casing sheet may consist of a non-woven material or like material, such as thermobonded spunbonded material or carded non-woven.

The absorbent pad enclosed between the casing sheets may consist of a cellulose fibre body which may or may not contain an addition of so-called superabsorbents and/or thermofibres. However, because the bodies 1, 2 shall be thin, it is preferred to mix superabsorbent particles with the cellulose fibres so as to increase the amount of liquid that can be absorbed, i.e. the maximum amount of liquid that can be absorbed in the absorbent pad. In such cases, an insulating layer can be placed conveniently between the inner casing sheet and the fibre body, partly to reduce the risk of rewetting and partly to increase the softness of that part of the napkin which lies closest to the wearer's body.

Naturally, the absorbent pad can be constructed in other ways without departing from the scope of the invention. For instance, the absorbent material in the absorbent pad may include solely superabsorbents disposed in or between appropriate diffusion layers.

Figure 2:
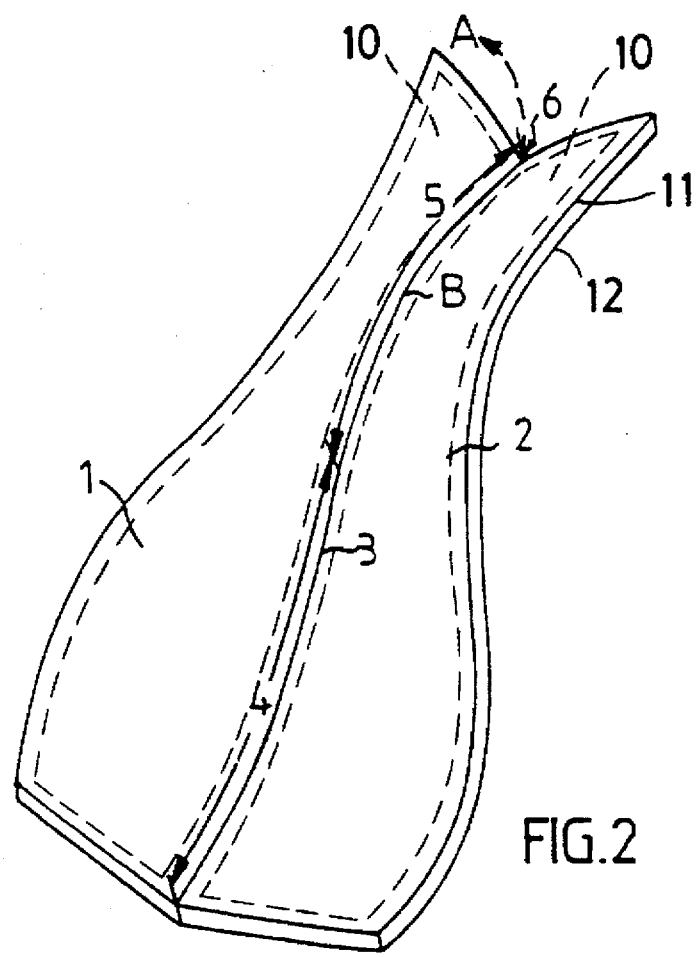
FIG. 2 is a perspective view obliquely from above which illustrates the article in FIG. 1 when un-folded.

FIG. 2 shows the napkin of FIG. 1 unfolded. As will be seen from FIG. 2, when the napkin is unfolded a cupped part is formed in the napkin within the region of the outwardly (downwardly in the Figures) convex section 4 of the S-shaped edge 3. It will also be seen that the article has a V-shaped cross-section within the region of the outwardly concave section 5 of the S-shaped edge.

Figure 3:
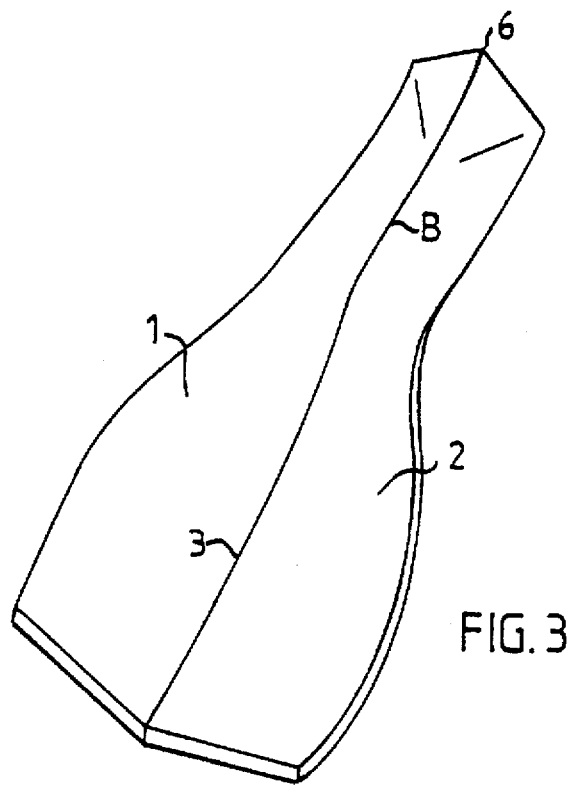
FIG. 3 is a view similar to the view of FIG. 2 and shows the article when ready for use.

FIG. 3 illustrates the napkin in its ready-for-use state, i.e. its state prior to being placed on the wearer's body. The configuration of the napkin in its state of use differs from the configuration achieved solely by folding out the napkin in that the downwardly extending end part (adjacent end 6) of the outwardly concave section 5 of the edge 3, as seen in FIGS. 1 and 2, is curved upwardly in the FIG. 3 configuration, and in that the napkin in cross-section has the shape of an inverted V within this part of the napkin. Furthermore, within the immediately following part of the section 5, the bodies 1, 2 are almost fully unfolded, i.e. the article is essentially flat within this part of the napkin.

Figure 4:
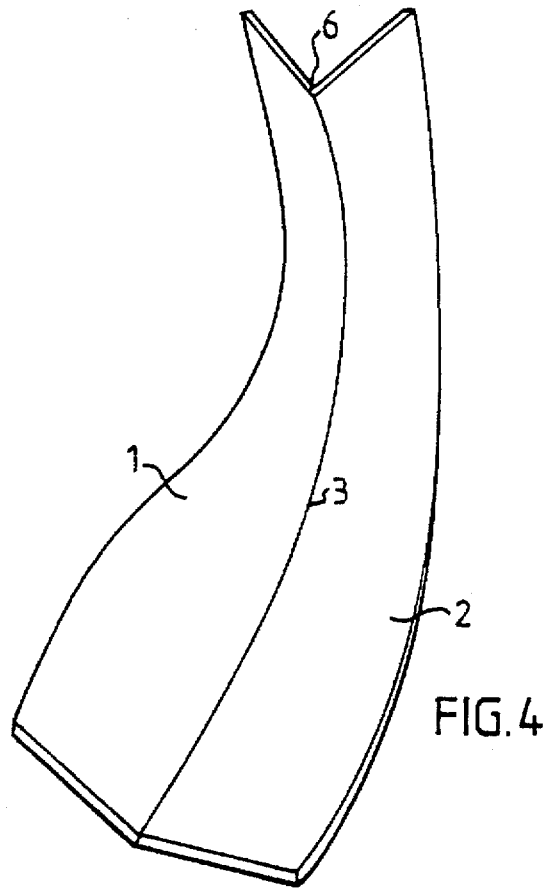
FIG. 4 is a view similar to the view of FIG. 2 and illustrates another conceivable shaped form of the article.

This upward bending of the edge 3 in the aforesaid end-part of the section 5 can be achieved with a simple hand movement, namely by placing a thumb on the point B in FIG. 2 and then pressing the end 6 of the edge 3 upwards with the index finger, as indicated by the broken arrow A. The end-part of the section 5 will then automatically be brought to the shape shown in FIG. 3, because this shape constitutes one of the stable shapes permitted by the geometrical configuration of the napkin. FIG. 4 illustrates another stable shape of the napkin, in which the whole of that section 5 of the edge 3 which was originally outwardly concave is curved upwards. It is also possible to give the napkin a stable shape when solely the forward part of the section 5 is curved upwards while the end-part of the section 5 has the shape shown in FIG. 2. It will be seen that the upwardly curved end-part of the section 5 in FIG. 3 can be given an appropriate size, by varying the curvature of the outwardly concave section 5 of the S-shaped edge. It will also be seen that by composing the outwardly concave section 5 of the edge 3 of portions of mutually different curvatures, optionally including straight parts, it is possible to provide an article which can be given a number of different stable shapes. The term "arcuate", as used herein, shall not therefore be given a limited interpretation and shall be considered to include a composite curve form of the outwardly concave section 5 of the edge 3.

It should be mentioned in this connection that the outwardly convex shape of the edge 3 within section 4 is not a necessary feature of the invention and that this edge section may conceivably have other shapes, such as a straight shape for instance. The illustrated shape is preferred, however, since the resultant cupped shape of the forward part of the napkin provides a particularly good body fit.

It will be seen from FIG. 3 that the point B lies forwardly of the upwardly curved part of the edge section 5, which is appropriate. Seen generally, however, this is not a prerequisite for automatically obtaining the napkin configuration shown in FIG. 3 as the end 6 of the edge 3 is curved upwards. When the stiffness of the outer casing sheet of the napkin approaches the limit at which the article is shaped stable, however, the point B must lie forwardly of the upwardly curved part of the section 5 in FIG. 3, in order to obtain the desired shape. Furthermore, it maybe necessary to place the index finger on the underside of the napkin opposite the point B and opposite the thumb, and then move the index finger backwards and upwards. A similar hand movement is also necessary in obtaining the shape shown in FIG. 4.

In the described embodiment of the invention, the requisite rigidity of the body is obtained by means of the outer casing sheet which supports the absorbent pad and the inner casing sheet and imparts shape stability to the composite body. It will be understood, however, that it is the total rigidity and flexibility of the composite bodies included in the article that are of significance. It is therefore possible within the scope of the present invention to utilize, for instance, an outer casing sheet of conventional kind which lacks essential stiffness and to provide the absorbent pad sandwiched between the casing layers with the requisite stiffness and flexibility, either by using suitable inserts or the like, or even by providing an absorbent pad in which has these properties are intrinsic. In the foregoing, the invention has been described with reference to a sanitary napkin in which the upwardly curved end-part of the napkin with its inverted-V form enables the article to be fitted conformingly to the region between the buttocks of the wearer. It will be understood, however, that the inventive principle can also be applied to other absorbent disposable articles. For instance, the configuration illustrated in FIG. 4 may be suitable for the crotch and rear part of a disposable diaper. It will be understood that when the invention is applied to diapers, which extend further up the back of the wearer than does a sanitary napkin, the rear part of the diaper will not be terminated with an outwardly concave part. In order to ensure that the V-shape illustrated in FIG. 3 can be obtained in the case of diapers, the diaper should be provided with two sequential outwardly concave sections in the area intended so as to form two opposing V-shaped regions which together form a pyramid when the concave parts of the diaper are curved upwardly in a manner similar to that described with reference to FIGS. 1–3.

The invention thus provides an absorbent disposable article which can be manufactured and packaged in a flat state and used in a three-dimensional state while ensuring that the article will fit conformingly to the body of the wearer. When taken together, these properties of the inventive article enable the article to be manufactured at a reasonable cost and therewith retailed at a reasonable price.

Figure 5:
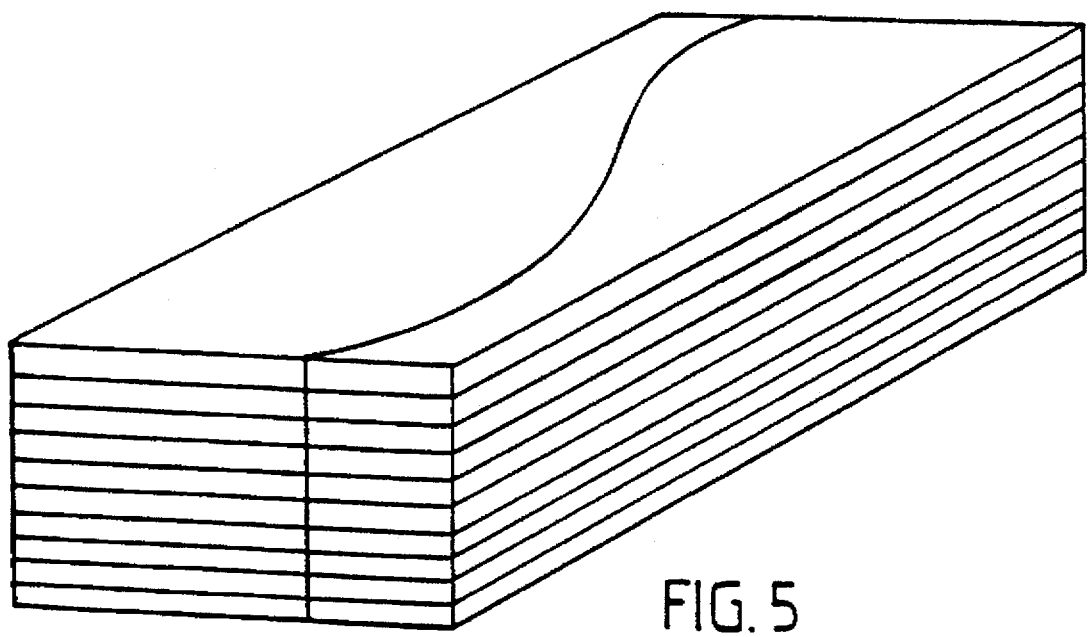
FIG. 5 illustrates in perspective a packaging stack of articles shown in FIG. 1.

Articles having the configuration illustrated in FIG. 1 and comprising two mirror-symmetrical bodies having a common S-shaped edge can be packaged in a particularly space-saving fashion when the two arcuate sections forming the S-shape are mirror-symmetrical in relation to a line that passes through the ends of the S, by placing the articles side-by-side in the manner shown in FIG. 5, i.e. with the convex section of one article being placed in the concave section of the other article. The stack of articles shown in FIG. 5 is placed in a bag or some like packaging medium.

I claim:

1. An absorbent disposable article, comprising:

at least two generally flat, flexible bodies, each of the bodies having a flat side for facing toward a wearer when the article is in use;

the bodies include absorbent material;

in a packaging state the flat sides of the bodies lie against one another;

the at least two bodies of the article are mutually joined along a common edge which forms a folding line around which the bodies can be unfolded from their packaging state; and the common edge includes a first arcuate section which, in the packaging state of the article, is arched toward a second opposing edge of each of the bodies.

2. An article according to claim 1, wherein the bodies are mirror-symmetrical in a longitudinal direction of the article.

3. An article according to claim 2, wherein the common edge of the bodies is S-shaped.

4. An article according to claim 3, wherein the bodies are comprised of an outer, liquid-impermeable casing material, an inner, liquid-permeable casing material which is intended to lie nearest the wearer's body when the article is in use, and said absorbent material is in the form of an absorbent pad enclosed between the casing sheets.

5. An article according to claim 2, wherein the bodies are comprised of an outer, liquid-impermeable casing material, an inner, liquid-permeable casing material which is intended to lie nearest the wearer's body when the article is in use, and said absorbent material is in the form of an absorbent pad enclosed between the casing sheets.

6. An article according to claim 5, wherein the bodies are mirror-symmetrical, the common edge is S-shaped, and the common edge includes a second arcuate section, the first arcuate section and the second arcuate section forming the S-shape and being mirror-symmetrical in relation to a line passing through ends of the sections.

7. An article according to claim 2, wherein the bodies are mirror-symmetrical, the common edge is S-shaped, and the common edge includes a second arcuate section, the first arcuate section and the second arcuate section forming the S-shape and being mirror-symmetrical in relation to a line passing through ends of the sections.

8. An article according to claim 1, wherein the common edge of the bodies is S-shaped.

9. An article according to claim 8, wherein the bodies are comprised of an outer, liquid-impermeable casing material, an inner, liquid-permeable casing material which is intended to lie nearest the wearer's body when the article is in use, and said absorbent material is in the form of an absorbent pad enclosed between the casing sheets.

10. An article according to claim 1, wherein the bodies are comprised of an outer, liquid-impermeable casing material, an inner, liquid-permeable casing material which is intended to lie nearest the wearer's body when the article is in use, and said absorbent material is in the form of an absorbent pad enclosed between the casing sheets.

11. An article according to claim 10, wherein the bodies are mirror-symmetrical, the common edge is S-shaped, and the common edge includes a second arcuate section, the first arcuate section and the second arcuate section forming the S-shape and being mirror-symmetrical in relation to a line passing through ends of the sections.

12. An article according to claim 1, wherein the bodies are mirror-symmetrical, the common edge is S-shaped, and the common edge includes a second arcuate section, the first arcuate section and the second arcuate section forming the S-shape and being mirror-symmetrical in relation to a line passing through ends of the sections.

* * * * *